United States Patent
Eberhard et al.

(10) Patent No.: US 7,244,063 B2
(45) Date of Patent: Jul. 17, 2007

(54) METHOD AND SYSTEM FOR THREE DIMENSIONAL TOMOSYNTHESIS IMAGING

(75) Inventors: Jeffrey Wayne Eberhard, Albany, NY (US); Bernhard Erich Hermann Claus, Niskayuna, NY (US); Abdulrahman Abdallah Al-Khalidy, Clifton Park, NY (US); Abdalmajeid Musa Alyassin, Niskayuna, NY (US); John Kaufhold, Altamont, NY (US); Gulnar Siddiqi, Milwaukee, WI (US)

(73) Assignee: General Electric Company, Niskayuna, NY (US)

( * ) Notice: Subject to any disclaimer, the term of this patent is extended or adjusted under 35 U.S.C. 154(b) by 429 days.

(21) Appl. No.: 10/739,541

(22) Filed: Dec. 18, 2003

(65) Prior Publication Data

US 2005/0133706 A1    Jun. 23, 2005

(51) Int. Cl.
*H05G 1/02*    (2006.01)
*A61B 6/08*    (2006.01)

(52) U.S. Cl. .................. 378/196; 378/197; 378/205

(58) Field of Classification Search ............ 378/4, 378/19–27, 196, 197
See application file for complete search history.

(56) References Cited

U.S. PATENT DOCUMENTS

| | | | | |
|---|---|---|---|---|
| 4,894,855 A | * | 1/1990 | Kresse | ............... 378/196 |
| 6,200,024 B1 | * | 3/2001 | Negrelli | ............... 378/197 |
| 6,292,531 B1 | | 9/2001 | Hsieh | |
| 6,435,715 B1 | * | 8/2002 | Betz et al. | ............... 378/197 |
| 7,110,490 B2 | | 9/2006 | Eberhard et al. | |
| 2003/0142790 A1 | * | 7/2003 | Zhou et al. | ............... 378/119 |
| 2005/0002550 A1 | | 1/2005 | Jabri et al. | |
| 2006/0291711 A1 | | 12/2006 | Jabri et al. | |

OTHER PUBLICATIONS

J.T. Dobbins, et al, "Tomosynthesis for improved pulmonary nodule detection", RSNA abstract No. 605, vol. 290, p. 280, 1998.
K.R. Maravilla, et al, "Digital Tomosynthesis: Technique for Electronic Reconstructive Tomography", AJNR:4, pp. 883-888, 1983.
U.S. Appl. No. 11/511,644, filed Aug. 29, 2006, Eberhard et al.

* cited by examiner

*Primary Examiner*—Edward J. Glick
*Assistant Examiner*—Irakli Kiknadze
(74) *Attorney, Agent, or Firm*—Fletcher Yoder (57) ABSTRACT

An imaging system for scanning a volume of interest in an object, the system includes a radiation source configured to traverse in a plurality of focal spot positions yielding a plurality of focal spot trajectories. Each focal spot trajectory defines a two dimensional focal spot projection in an image acquisition plane. Each of the focal spot positions comprise at least two positions at unequal distances from the image acquisition plane.

61 Claims, 11 Drawing Sheets

METHOD AND SYSTEM FOR THREE DIMENSIONAL TOMOSYNTHESIS IMAGING

BACKGROUND OF THE INVENTION

The present invention relates generally to the field of imaging, and more specifically to the field of tomosynthesis. In particular, the invention relates to tomosynthesis systems and methods employing new scanning trajectories for an x-ray source and a detector to yield an improved image of an object.

Tomography is well known for both industrial and medical applications. Conventional tomography is based on a relative motion of the x-ray source, the detector and the object. Typically, the x-ray source and the detector are either moved synchronously on circles or are simply translated in opposite directions. Due to that correlated motion, the location of the projected images of points within the object moves also. Only points from a particular slice, typically called a focal slice, will be projected always at the same location onto the detector and therefore imaged sharply. Object structures above and below the focal slice will be permanently projected at different locations. Because of that, they are not imaged sharply and will be superimposed as a background intensity to the focal slice. This principle of creating a 3D image with one slice in focus (focal slice) using a discrete number of projections is called tomosynthesis.

Tomosynthesis systems for medical applications, typically use an x-ray source for producing a fan or cone-shaped x-ray beam that is collimated and passes through the patient to then be detected by a set of detector elements. The detector elements produce a signal based on the attenuation of the x-ray beams. The signals may be processed to produce a radiographic projection. The source, the patient, or the detector are then moved relative to one another for the next exposure, typically by moving the x-ray source, so that each projection is acquired at a different angle.

By using reconstruction techniques, such as filtered back-projection, the set of acquired projections may then be reconstructed to produce diagnostically useful three dimensional images. Because the three dimensional information is obtained digitally during tomosynthesis, the image can be reconstructed in whatever viewing plane the operator selects. Typically, a set of slices representative of some volume of interest of the imaged object is reconstructed, where each slice is a reconstructed image representative of structures in a plane that is parallel to the detector plane, and each slice corresponds to a different distance of the plane from the detector plane.

In addition, because tomosynthesis reconstructs three dimensional data from projections, it provides a fast and cost-effective technique for removing superimposed anatomic structures and for enhancing contrast in in-focus planes as compared to the use of a single x-ray radiograph. Further, because the tomosynthesis data consists of relatively few projection radiographs that are acquired quickly, often in a single sweep of the x-ray source over the patient, the total x-ray dose received by the patient is comparable to the dose of a single conventional x-ray exposure and is typically significantly less than the dose received from a computed tomography (CT) examination. In addition, the resolution of the detector employed in tomosynthesis is typically greater than the resolution of detectors used in CT examinations. These qualities make tomosynthesis useful for such radiological tasks as detecting pulmonary nodules or other difficult to image pathologies.

Though tomosynthesis provides these considerable benefits, the techniques associated with tomosynthesis also have disadvantages.

Reconstructed data sets in tomosynthesis often exhibit a blurring of structures in the direction of the projections that were used to acquire the tomosynthesis data. This is expressed in a poor depth resolution of the 3D reconstruction or depth blurring. The degree of depth blurring depends on the scanning parameters, the distance of the object from the plane of interest, and on the size and orientation of the object relative to the scan paths. For example, the traditionally used linear scanning trajectory may lead to a limited z-resolution, and a contrast that may depend on the orientation of the anatomy to be imaged, while the circular trajectory may lead to circular artifacts, caused by out-of-plane structures, that may be mistaken for pathology. The blurring of structures may create undesirable image artifacts and inhibit the separation of structures located at different heights in the reconstruction of the imaged volume. Some existing tomosynthesis reconstruction algorithms address streaking artifacts due to acquisition at discrete focal spot locations, but do not address depth blurring.

Also generally, the solid angular range and complexity of the acquisition projection geometries trade off against the physical limitations of an exam. For example, projection geometries which result from simple linear focal spot trajectories using a flat fixed detector over a small angular range are faster and less demanding of the focal spot positioning apparatus. The smaller exam time mitigates patient motion artifacts for medical imaging applications. However, because the angular range of these projection geometries is small, depth blurring will be more severe in volume reconstructions of objects imaged using such an acquisition configuration. Projection geometries which result from more complex three dimensional focal spot trajectories over a larger solid angular range where a custom geometry multiple surface detector may be repositioned during the scan require a longer exam time, demand more of the focal spot positioning apparatus, demand more of the detector positioning apparatus, and may require additional design considerations for the detector shape. The longer exam time exacerbates patient motion artifacts for medical imaging applications. However, because the solid angular range of these projection geometries is larger, the depth blurring artifacts in the reconstructed volume will be reduced relative to the simpler scan.

Therefore there exists a need to adapt the current tomosynthesis systems to provide for new scanning trajectories to address the depth blurring of the imaged object by using more general projection geometries that may be more suited to reconstructing the region of interest and the anatomy to be imaged.

BRIEF DESCRIPTION OF THE INVENTION

Briefly, in accordance with one aspect of the present invention, an imaging system for scanning a volume of interest in an object, the system includes a radiation source configured to traverse in a plurality of focal spot positions yielding a plurality of focal spot trajectories. Each of the focal spot trajectory defines a two dimensional focal spot projection in an image acquisition plane. The focal spot positions include at least two positions at unequal distances from the image acquisition plane.

In accordance with another aspect of the invention, a method for scanning a volume of interest in an object using an imaging system, the method includes traversing a radiation source in a plurality of focal spot positions yielding a plurality of focal spot trajectories, each focal spot trajectory defines a two dimensional focal spot projection in an image acquisition plane, and the focal spot positions includes at least two positions at unequal distances from the image acquisition.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
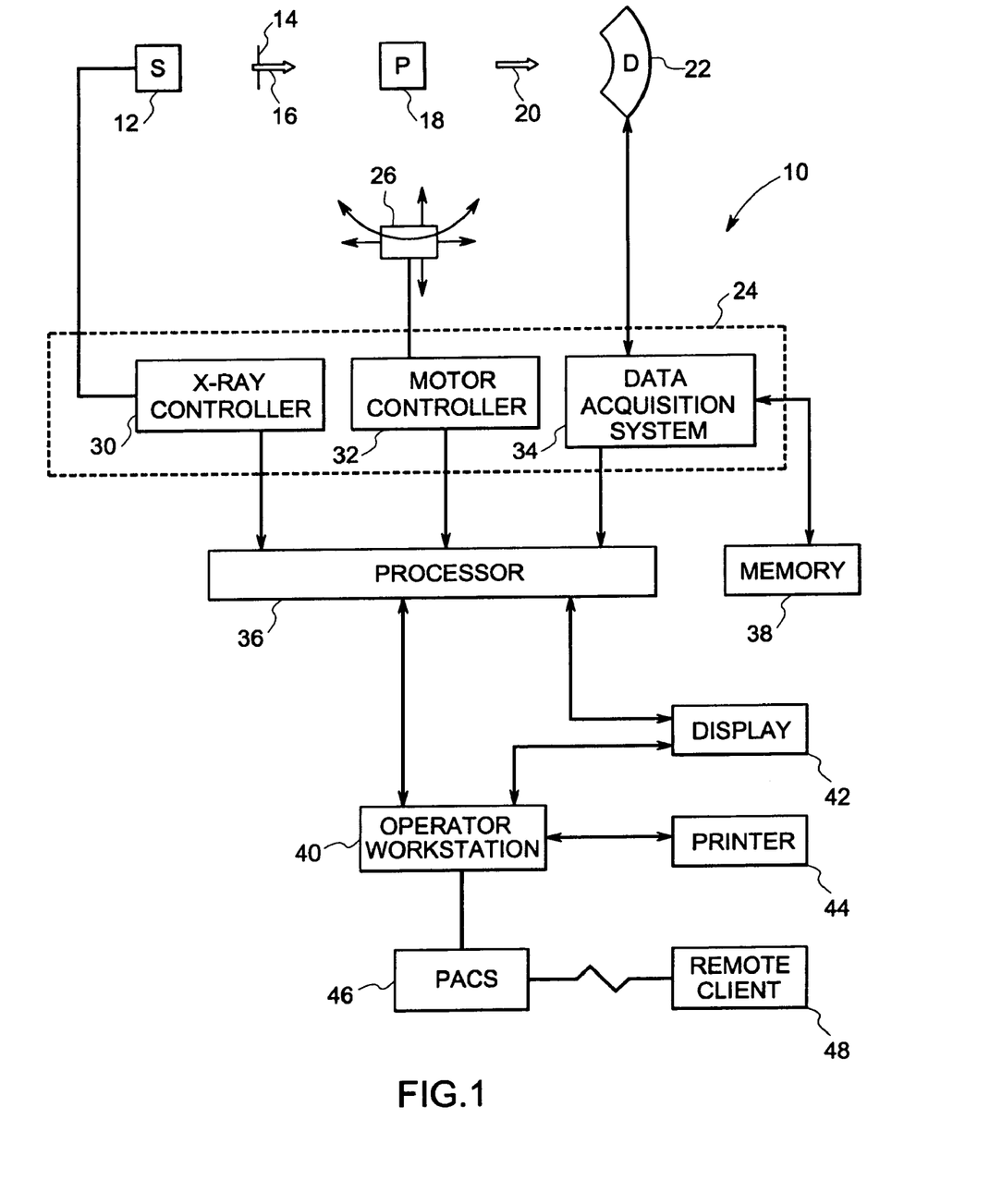
FIG. 1 is a diagrammatical view of an exemplary imaging system in the form of a tomosynthesis system for scanning an object in accordance with aspects of the present technique.

FIG. 1 illustrates diagrammatically an imaging system 10 which may be used for acquiring and processing image data. In the illustrated embodiment, the system 10 is a tomosynthesis system designed both to acquire original image data, and to process the image data for display and analysis in accordance with the present technique. In the embodiment illustrated in FIG. 1, the imaging system 10 includes a source 12 of radiation which is typically x-ray radiation in tomosynthesis, the source 12 is freely movable in three dimensions with respect to the object 18 and a detector 22. In this exemplary embodiment, the x-ray radiation source 12 typically includes an x-ray tube and associated support and filtering components.

A stream of radiation 16 is emitted by the source 12 and impinges an object 18, for example, a patient in medical applications. A portion of the radiation 20 passes through or around the object and impacts a detector array, represented generally at reference numeral 22. Detector elements of the array produce electrical signals that represent the intensity of the incident x-ray beam. These signals are acquired and processed to reconstruct an image of the features within the object. A collimator 14 may define the size and shape of the x-ray beam 16 that emerges from the x-ray source 12.

Source 12 is controlled by a system controller 24 which furnishes both power and control signals for tomosynthesis examination sequences, including positioning of the source 12 relative to the object 18 and the detector 22. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a positional subsystem 26 which positions the x-ray source 12 relative to the object 18 and the detector 22. In alternative embodiments the positional subsystem 26 may move the detector 22 or even the object 18 instead of the source 12 or together with the source 12. In yet another embodiment, more than one component may be movable, controlled by positional subsystem 26. Thus, radiographic projections may be obtained at various angles through the object 18 by changing the relative positions of the source 12, the object 18, and the detector 22 via the positional subsystem 26 according to various embodiments illustrated hereinbelow in detail.

Additionally, as will be appreciated by those skilled in the art, the source of radiation may be controlled by an x-ray controller 30 disposed within the system controller 24. Particularly, the x-ray controller 30 is configured to provide power and timing signals to the x-ray source 12. A motor controller 32 may be utilized to control the movement of the positional subsystem 26.

Further, the system controller 24 is also illustrated comprising a data acquisition system 34. The detector 22 is typically coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor 36.

The processor 36 is typically coupled to the system controller 24. The data collected by the data acquisition system 34 may be transmitted to the processor 36 and moreover, to a memory 38. It should be understood that any type of memory adapted to store a large amount of data may be utilized by such an exemplary system 10. Also the processor 36 is configured to receive commands and scanning parameters from an operator via an operator workstation 40, typically equipped with a keyboard and other input devices. An operator may control the system 10 via the input devices. Thus, the operator may observe the reconstructed image and other data relevant to the system from processor 36, initiate imaging, and so forth.

A display 42 coupled to the operator workstation 40 may be utilized to observe the reconstructed image and to control imaging. Additionally, the image may also be printed on to a printer 44 which may be coupled to the processor 36 and the operator workstation 40. Further, the operator workstation 40 may also be coupled to a picture archiving and communications system (PACS) 46. It should be noted that PACS 46 may be coupled to a remote system 48, radiology department information system (RIS), hospital information system (HIS) or to an internal or external network, so that others at different locations may gain access to the image and to the image data.

It should be further noted that the processor 36 and operator workstation 46 may be coupled to other output devices which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
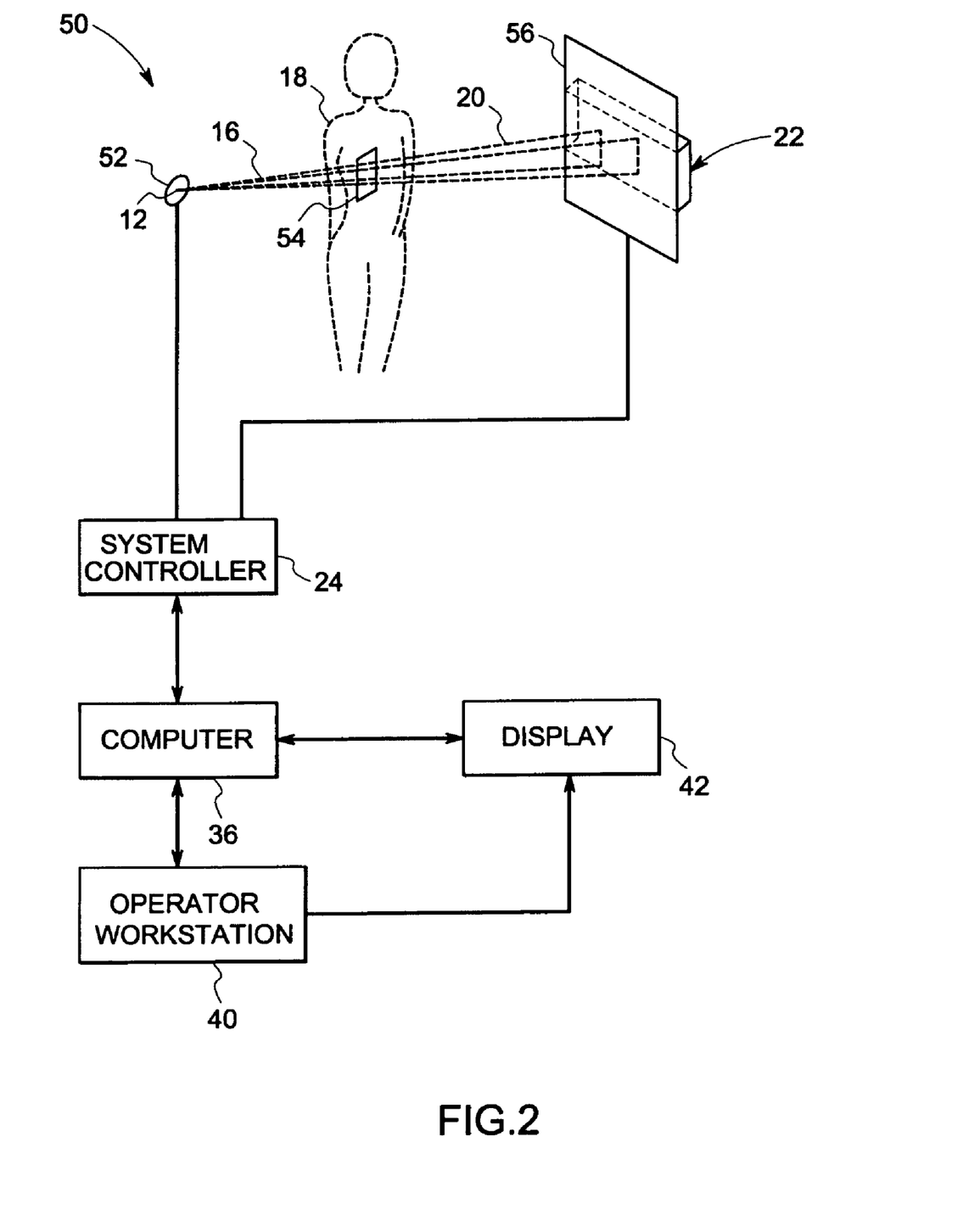
FIG. 2 is a diagrammatical view of a physical implementation of the tomosynthesis system of FIG. 1.

Referring generally to FIG. 2, an exemplary imaging system utilized in a present embodiment may be a tomosynthesis imaging system 50. In an arrangement similar to that described above, the tomosynthesis imaging system 50 is illustrated with a source 12 and a detector 22 between which an object, illustrated as a patient 18 may be disposed. The source of radiation 12 typically includes an x-ray tube which emits x-ray radiation from a focal point 52. The stream of radiation is directed towards a particular region 54 of the patient 18. It should be noted that the particular region 54 of the patient 18 is typically chosen by an operator so that the most useful scan of a region may be made.

In a typical operation, x-ray source 12 is positioned at a predetermined distance above the patient 18 and projects an x-ray beam from the focal point 52 and toward detector array 22. The x ray source is configured to move in a plurality of focal spot positions. In specific embodiments, the source is configured to move in first and second dimensions generally parallel to the plane 56 of the detector 22 and in a third dimension generally perpendicular to the plane 56 of the detector 22. The detector 22 is disposed in a spaced apart relationship with respect to the source 12 and at a predetermined distance from the patient 18. The detector in one embodiment is kept stationary. Another embodiment includes detector movement and is described in detail hereinbelow. The region of interest 54 or anatomy to be imaged is placed between the x-ray detector 22 and a plurality of x-ray focal spot positions 52 (described in greater detail in the description of FIG. 3), and the focal spot is scanned to other positions consistent with image acquisition time, dose, signal to noise ratio, and mechanical complexity requirements. The detector 22 is generally formed by a plurality of detector elements, generally corresponding to pixels, which sense the x-rays that pass through and around a object of interest 54, such as particular body parts, for instance the chest, lungs and so on. In one embodiment, the detector 22 consists of a 2,048×2,048 rectangular array of elements which correspond to a pixel size of 200 μm×200 μm, though other configurations and sizes of both detector 22 and pixel are of course possible. Each detector element produces an electrical signal that represents the intensity of the x-ray beam at the position of the element at the time the beam strikes the detector. The movement of the x-ray source is described in detail with reference to the discussion of FIG. 3–FIG. 14 hereinbelow. In one embodiment the distance between the source 12 and the detector 22 is approximately 180 cm and the total range of motion of the source 12 is between 31.5 cm and 131 cm, which translates to ±5° to ±20° where 0° is a centered position. In this embodiment, typically at least 11 projections are acquired, covering the full angular range.

The processor 36 is typically used to control the entire tomosynthesis system 50. The main processor that controls the operation of the system may be adapted to control features enabled by the system controller 24. Further, the operator workstation 40 is coupled to the processor 36 as well as to a display, so that the reconstructed image may be viewed.

As the x-ray source 12 is moved in three-dimensions in reference to the plane 56 of detector, in accordance with the different embodiments described herein, the detector 22 collects data of the attenuated x-ray beams. Data collected from the detector 22 then typically undergo pre-processing and calibration to condition the data to represent the line integrals of the attenuation coefficients of the scanned objects. The processed data, commonly called projections, are then typically backprojected to formulate an image of the scanned area. In tomosynthesis, a limited number of projections are acquired, typically thirty or less, each at a different angle relative to the object and detector. Reconstruction algorithms are typically employed to perform the reconstruction on this data to reproduce the initial images.

Once reconstructed, the image produced by the system of FIGS. 1 and 2 reveals the three dimensional relationship of internal features of the patient 18. The image may be displayed to show these features and their three dimensional relationships. Though the reconstructed image may comprise a single reconstructed slice representative of structures at the corresponding location within the imaged volume, more than one slice is typical.

Figure 3:
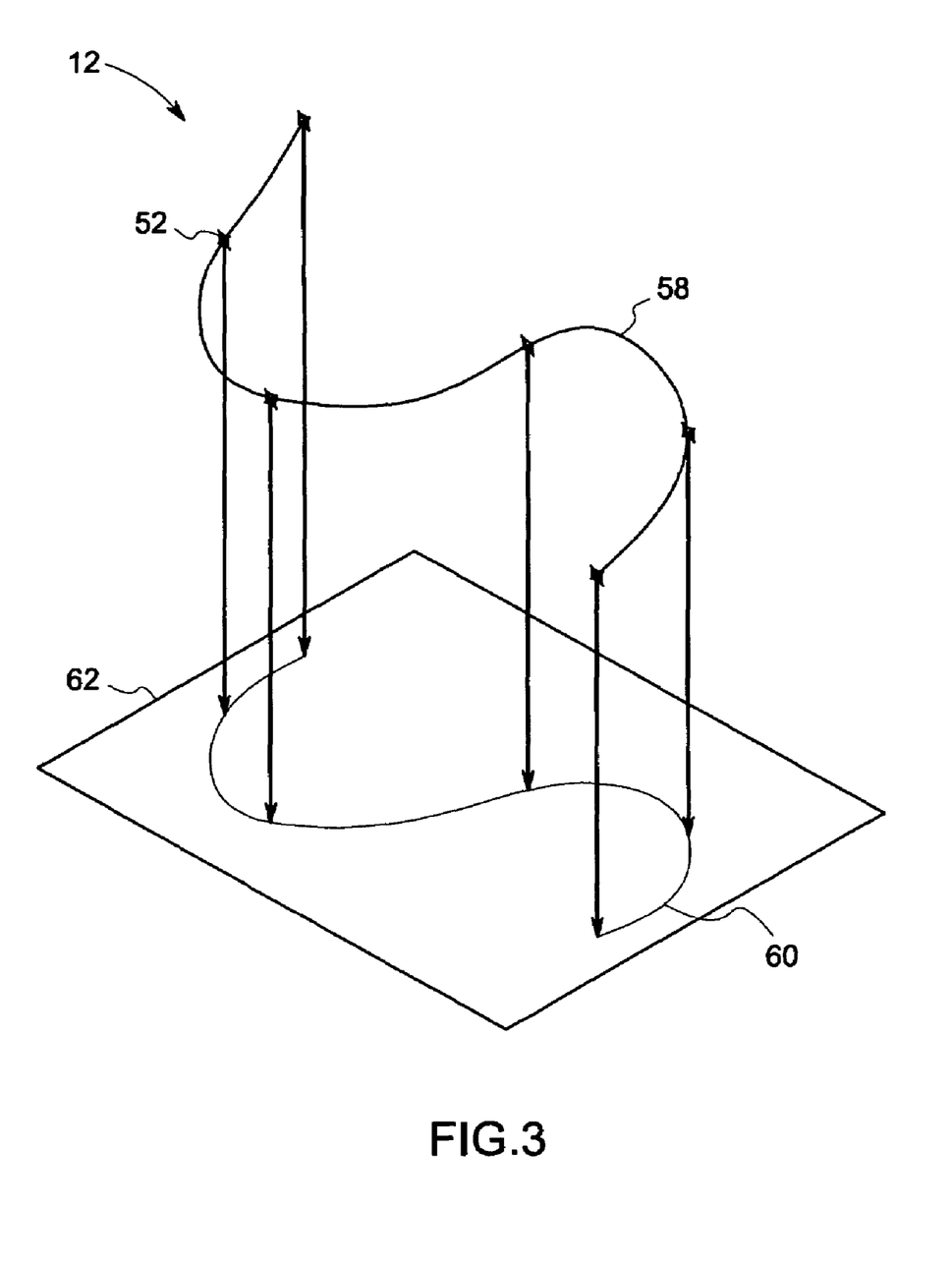
FIG. 3 is a top view of an embodiment of the present technique illustrating multiple source positions, a source trajectory and a parallel beam projection of the trajectory in an image acquisition plane.
Figure 4:
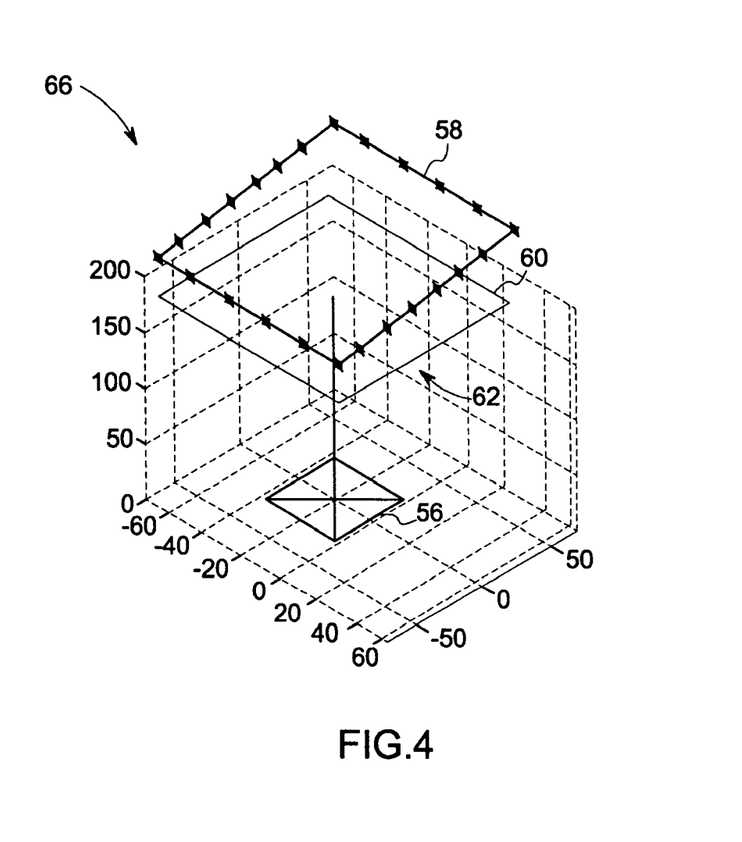
FIG. 4–FIG. 14 is a collection of top views illustrating different source trajectories and their projections in an image acquisition plane.
Figure 5:
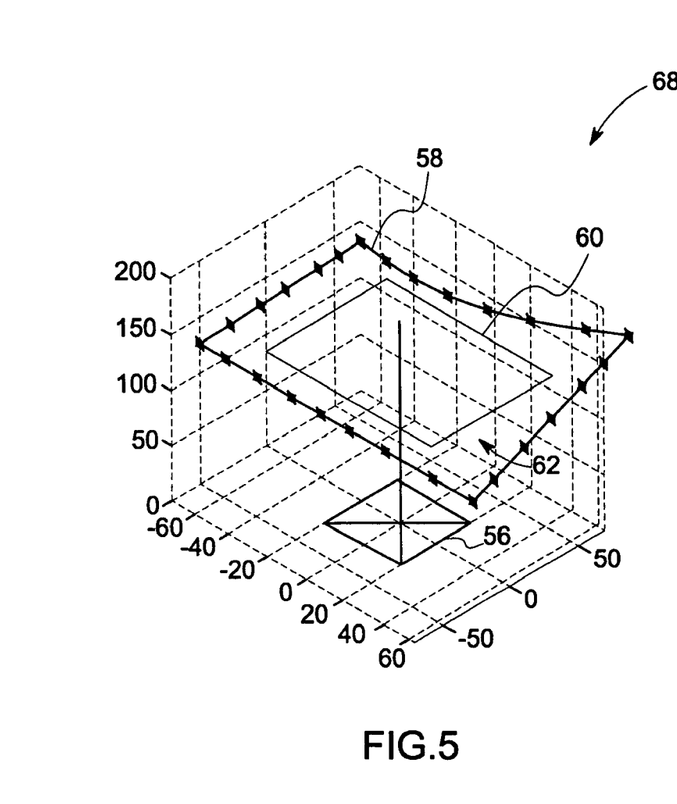
Figure 6:
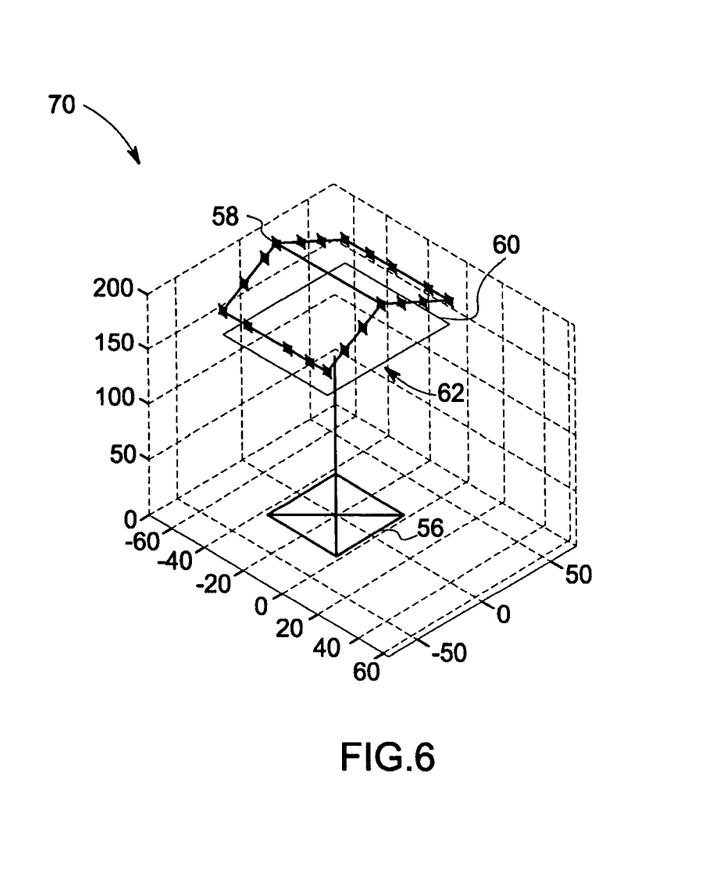
Figure 7:
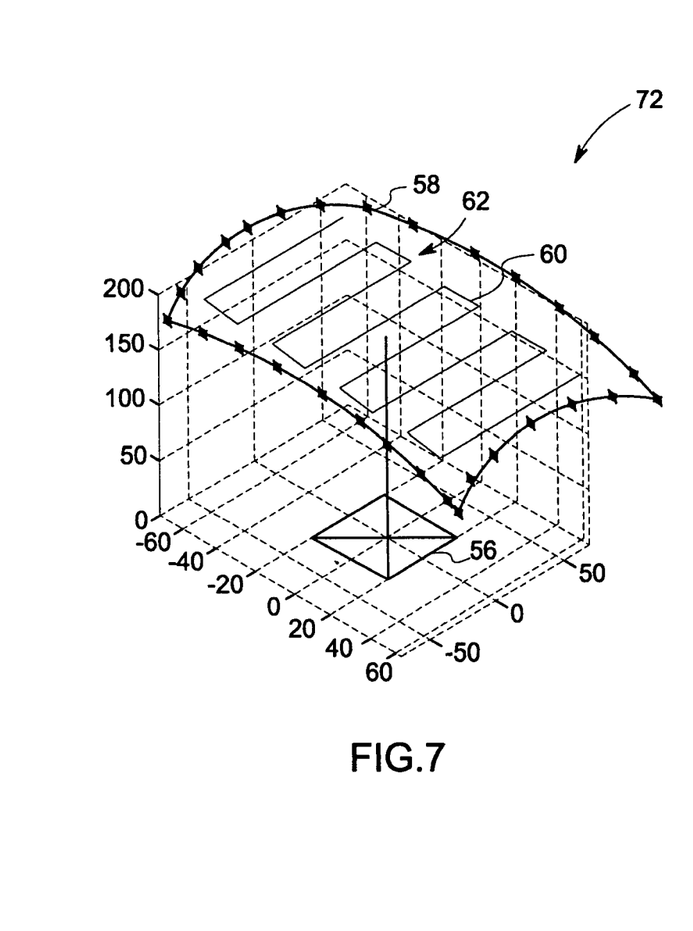
Figure 8:
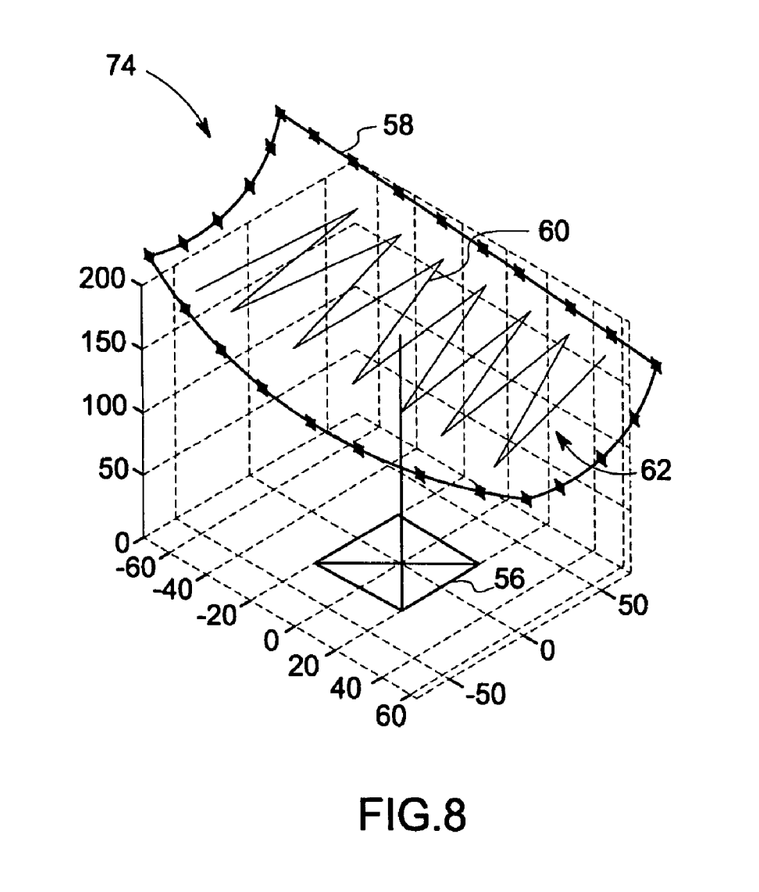
Figure 9:
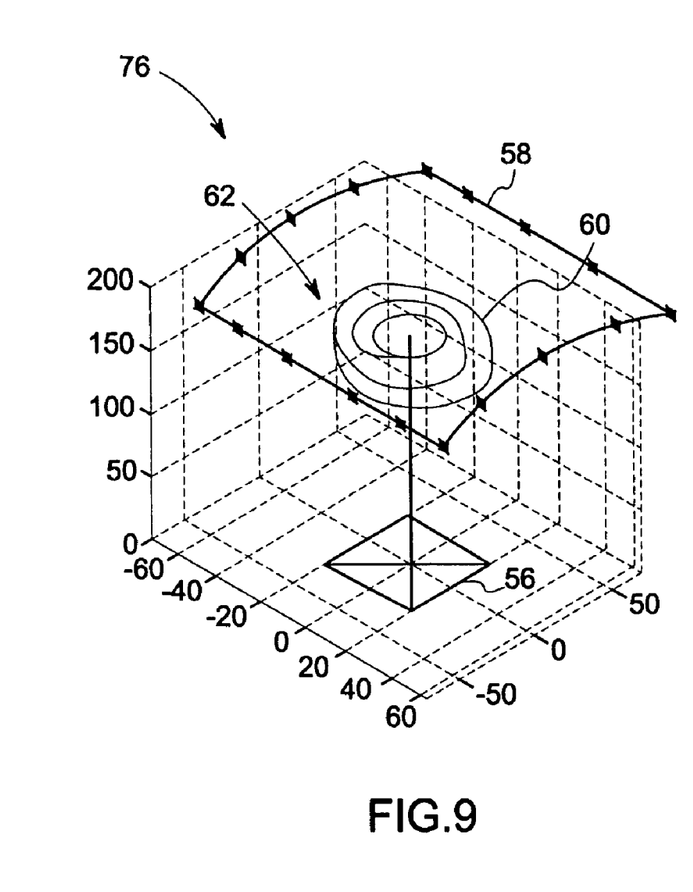
Figure 10:
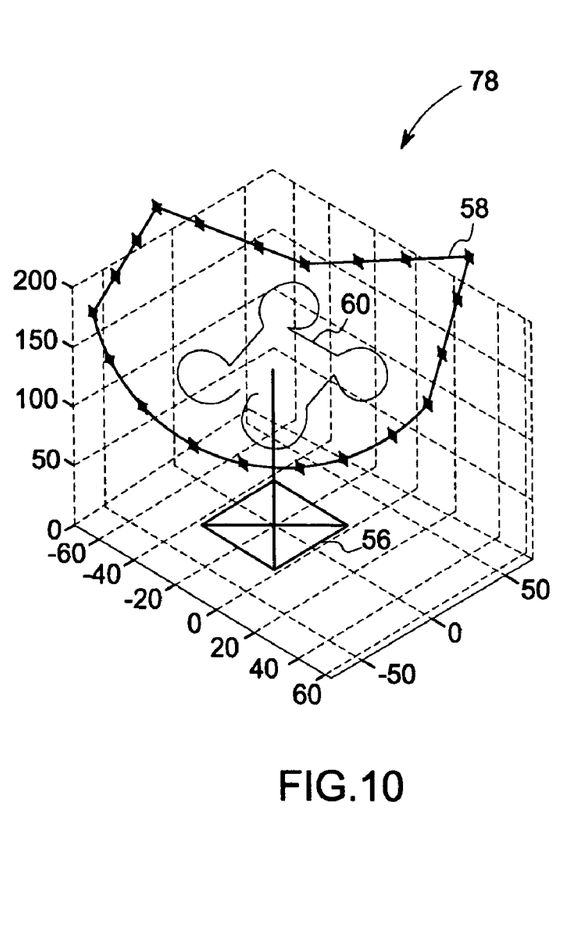
Figure 11:
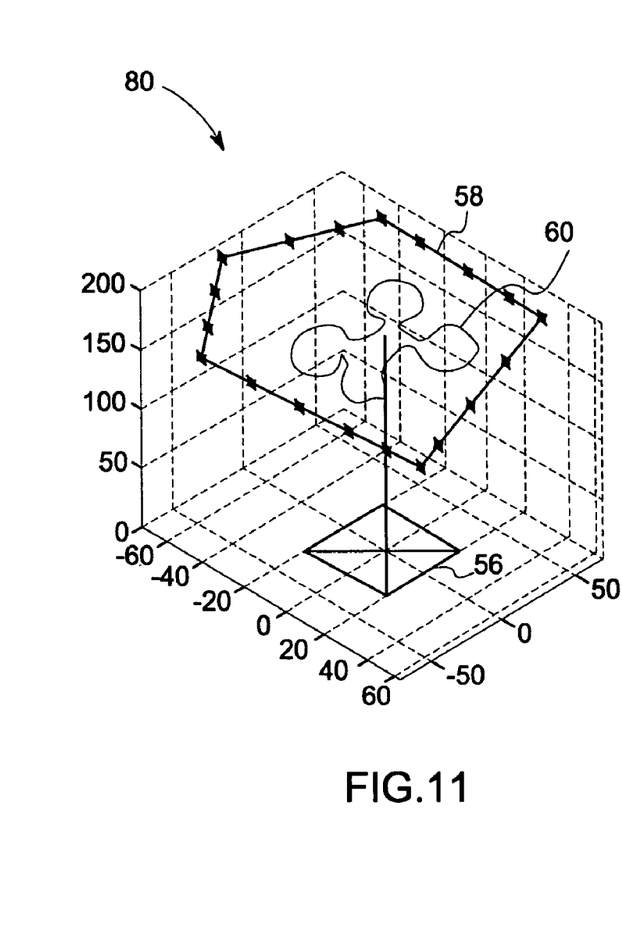
Figure 12:
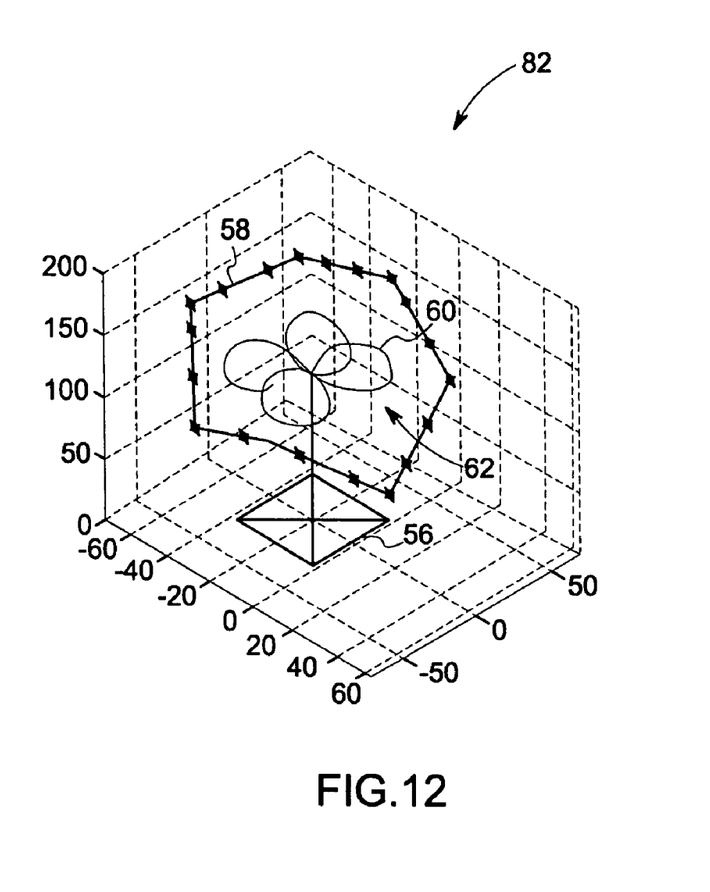
Figure 13:
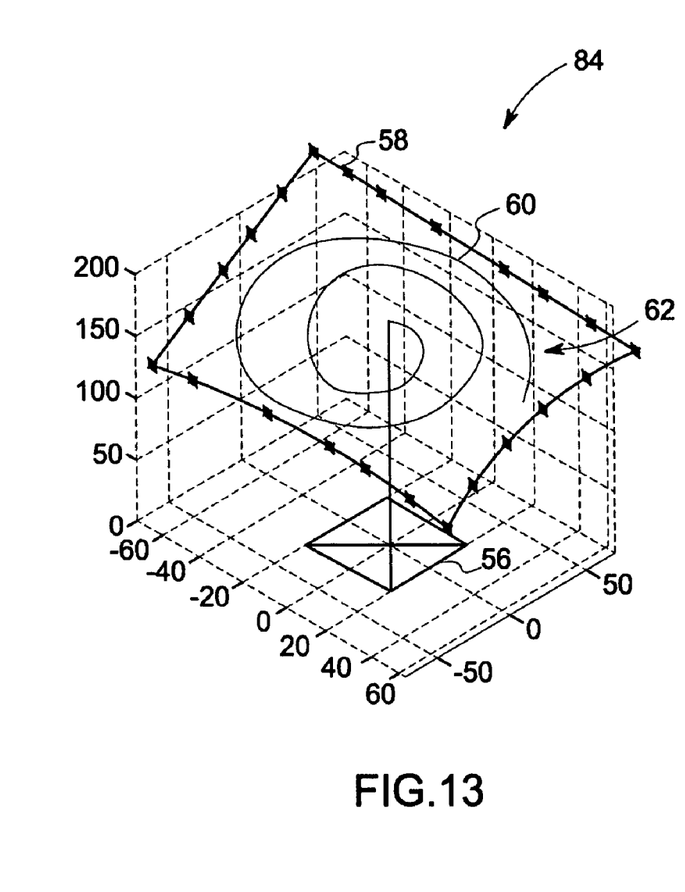
Figure 14:
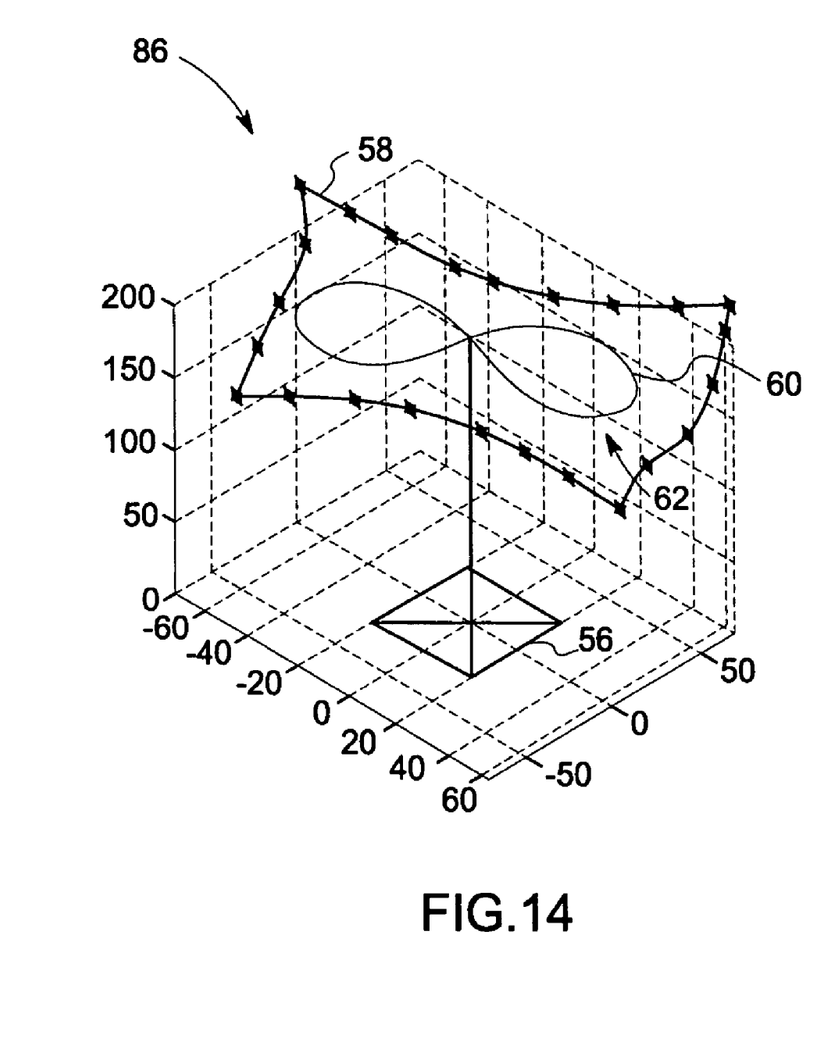

FIG. 3 illustrates an example of the source movement wherein the radiation source 12 is configured to traverse in a plurality of focal spot positions 52 yielding a plurality of focal spot trajectories 58. The focal spot trajectory 52 is defined as a curve traced out by joining the focal spot positions 52 from the start of the exam until the end of the exam (called total exam time). Further, each focal spot trajectory 58 defines a two dimensional focal spot projection 60 in an image acquisition plane 62. Thus the image acquisition plane 62 is defined as a plane which receives two dimensional projections of the three dimensional focal spot trajectories. The focal spot positions 52 comprise at least two positions at unequal distances from the image acquisition plane 62, thus defining a three dimensional movement of the source 12. FIG. 3 illustrates a specific embodiment using a parallel projection geometry. The two-dimensional curve 60 identifies the projection of the three dimensional trajectory 58, in one direction, onto an acquisition identification plane 62. In FIG. 3, the trajectory 58 is projected in the z dimension, but any direction can be used. Thus, for a given choice of acquisition identification plane 62, the focal spot trajectory 58 is identified as a two dimensional curve 60. This association between three dimensional scan trajectories and two dimensional curves in an image acquisition plane is independent of the detector. It would be appreciated by those skilled in the art that perspective projection geometries will be obtained if the image acquisition is from a perspective of a point within the object 18.

FIG. 4 through FIG. 14 illustrate a collection of exemplary top views depicted generally by reference numerals 66, 68, 70, 72, 74 76, 78, 80, 82, 84, and 86 showing different source trajectories 58 and their projections 60 in an image acquisition plane 62 in reference with the plane 56 of the detector 22. Non-limiting examples of focal spot positions 52 include focal spot positions spaced equally on the focal spot trajectory, the focal spot positions having equal angular increment along the focal spot trajectory. Similarly, the non-limiting examples for the focal spot projections include at least one of a circle, an ellipse, a square, a rectangle, a composition of at least two closed curves intersecting at a point, a composition of a set of non-intersecting closed curves, and a spiral in the image acquisition plane. More examples of the focal spot projections include a shape including at least one of a saw tooth curve, a sine wave, a square wave, or an arbitrary curve, wherein the amplitude of the shape is defined by the volume of interest being imaged.

Thus it would be appreciated by those skilled in the art that various configurations of source movements are possible yielding a number of three dimensional focal spot location trajectories which are associated with respective two dimensional projections. FIG. 4 through FIG. 14 are just illustrative example for few of these possibilities.

Non-limiting examples of source movement include a path aligned to match the volume of interest being imaged and a path aligned to match a selection of features of the volume of interest being imaged. For example, for an anatomy that is long in one direction, it is beneficial to scan in the perpendicular direction. Also, the angular range is chosen such as to achieve the required depth sharpness for the imaged anatomy. A larger angular range leads to a better depth sharpness. Furthermore, it may be useful to align the scanning trajectory with certain features of the anatomy. For example, in chest imaging, it may be advantageous to scan along multiple lines that are aligned with the long axes of the lungs. Furthermore, it may be beneficial to scale the scanning trajectory according to the size of the patient, or the size of the anatomy. In one embodiment, additional parameters that are needed for this optimization of the scanning trajectory can be derived from a single pre-shot of the anatomy. This trajectory may be derived in conjunction with a pre-existing model of the anatomy.

Also the source in one example is configured to traverse in at least one of a step and shoot mode and in a continuous mode. In step and shoot mode, the positional subsystem 26 moves the focal spot to the desired location 52 and then nominally stops moving. The electron beam then excites the anode at that focal spot location any number of times. Then the positional subsystem 26 moves the focal spot to a new position and acquires at the new position similarly, etc. In step and shoot mode, focal spot locations 52 are nominally fixed on the trajectory 58. In continuous mode, the positional subsystem 26 moves the focal spot through the nominal focal spot location 52 without stopping completely. In continuous mode, there may be some acceleration and/or deceleration of the focal spot near the nominal focal spot location. If the continuous mode is used, the detector 22 can be simultaneously moved in an effectively opposite direction to reduce motion blurring. In yet another example, the source is a distributed anode and the electron beam is steered toward a plurality of focal spot locations 52 on the distributed anode. In yet another example, the source is a distributed field emitter and the x-rays are directed at the detector from each source location. In a specific example, at least one radiation source 12 is configured to direct radiation toward a detector 22 through the subject of interest 18 from a plurality of focal spot positions 52 defining a desired two dimensional projection 60 in an image acquisition plane 62 as described hereinabove. The focal spot positions 52 are displaced from one another in first and second dimensions generally parallel with the image acquisition plane 62 at a distance from the image acquisition plane 62 in a third dimension. Similarly the focal spot positions 52 can be selected in a variety of ways to suit a particular exam or anatomy being imaged.

Figure 15:
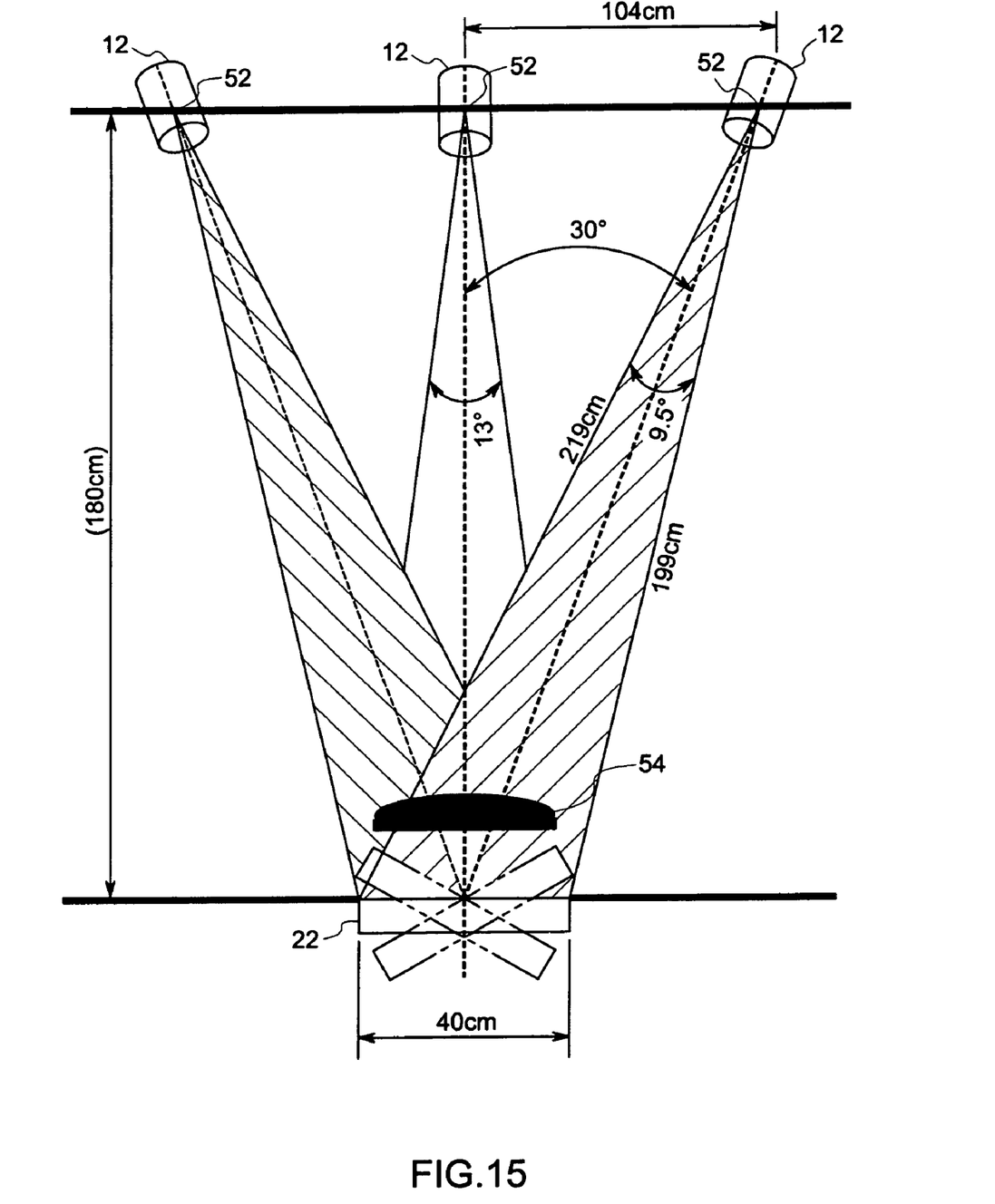
FIG. 15 is a diagrammatic view illustrating detector movement with respect to an X-ray source.
Figure 16:
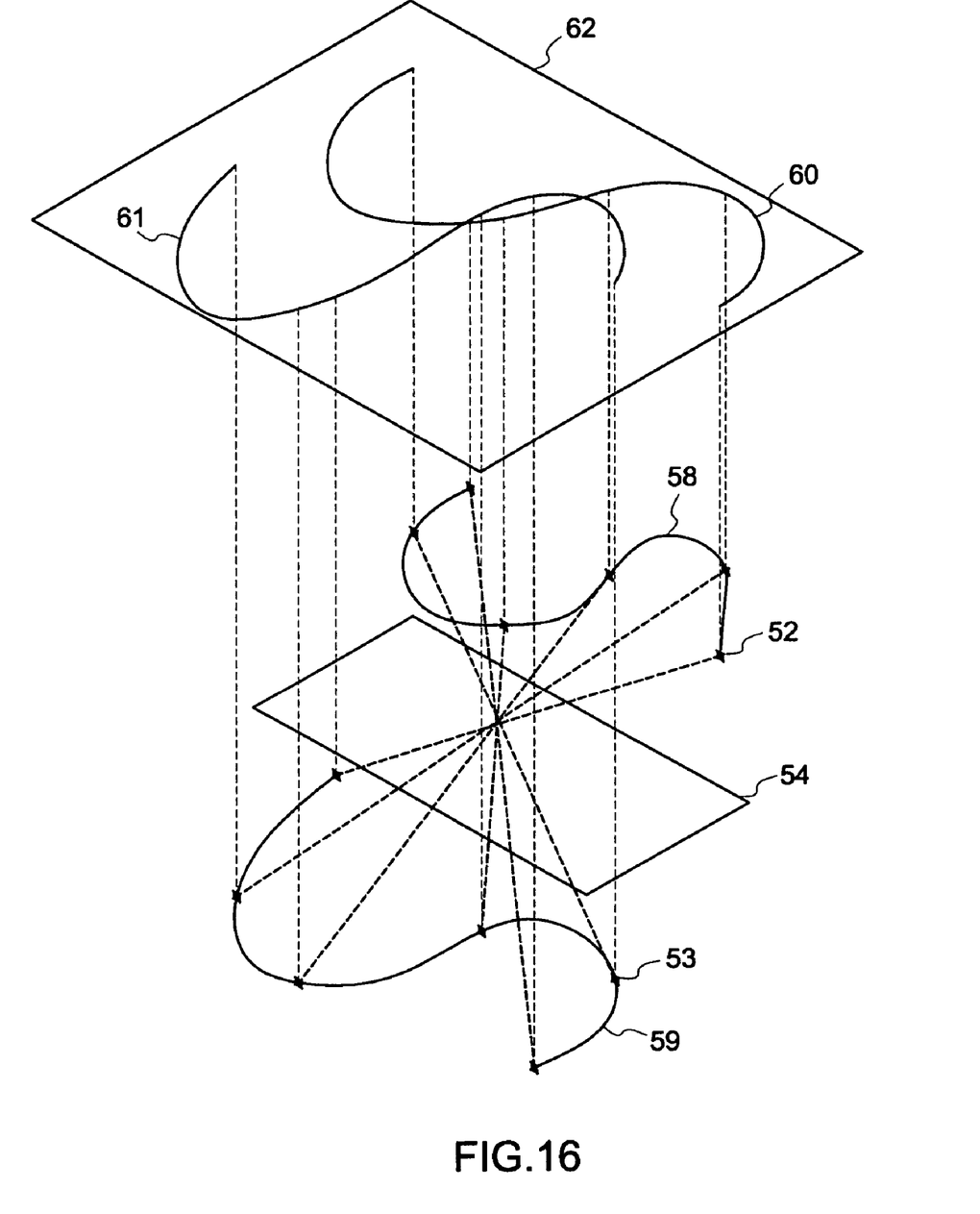
FIG. 16 is a top view illustrating the source and detector trajectories and their respective projections in an image acquisition plane.

Furthermore, in accordance with another embodiment, as illustrated in FIGS. 15 and 16, the detector 22 is traversed in a plurality of detector positions 53, that is, it is translated, tilted, and/or rotated, each of the detector positions 53 corresponds to a respective focal spot position 52. Referring to FIG. 16, repositioning the detector serves to keep the region of interest 54 centered on the detector 22. In another example the detector 22 is repositioned to limit the missing data from the region of interest 54. Referring to FIG. 16, the detector positions yield a detector trajectory 59 defining a two dimensional detector projection 61 in the image acquisition plane 62. The detector 22 in a specific embodiment is configured to move during imaging sequences in first and second dimensions in the plane 56 of the detector, and in a third dimension to vary the distance between the source 12 and the detector 22. The dynamic detector location, orientation or configuration in these embodiments is associated with a two dimensional projection 61. Thus a number of projection geometry trajectories, are defined as the coupled set of focal spot projection and detector projection, 60 and 61 respectively, for a given plane 62. As will be evident to those skilled in the art in the embodiments described hereinabove, the motion of the object 18 can be removed, that is, if the object 18 moves during the total exam time, the focal spot trajectory and the detector trajectory can be adjusted to effectively remove the relative motion of the object. This is possible because in the embodiments described hereinabove, the projection of a locus of points in the object on the detector remains stationary during the scan by adjusting the focal spot trajectory and the detector trajectory. The locus of points include but are not limited to a plane and a curved surface.

As would be appreciated by those skilled in the art the technique also includes the methods for scanning and acquiring images using the various embodiments of the invention described hereinabove.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An imaging system for scanning a volume of interest in an object, the system comprising:
   a radiation source configured to traverse in a plurality of focal spot positions yielding a plurality of focal spot trajectories, wherein each focal spot trajectory defines a two dimensional focal spot projection in an image acquisition plane, and wherein the focal spot positions comprise at least two positions at unequal distances from the image acquisition plane;
   a detector configured to acquire a plurality of acquisition images of the volume of interest in the object from the image acquisition plane, wherein the volume of interest is placed between the detector and the plurality of focal spot positions,
   wherein a projection of a locus of points in the object on the detector remains stationary during the scan by adjusting the focal spot trajectory and/or a detector trajectory.

2. The system of claim 1, wherein the source traverses a path aligned to match the volume of interest being imaged.

3. The system of claim 2, wherein the source traverses a path aligned to match a selection of features of the volume of interest being imaged.

4. The system of claim 1, wherein the source is configured to traverse in at least one of a step and shoot mode and a continuous mode.

5. The system of claim 1, wherein the source is a distributed anode.

6. The system of claim 1, wherein the source is a distributed field emitter.

7. The system of claim 1, wherein the focal spot positions are spaced equally on the focal spot trajectory.

8. The system of claim 7, wherein the focal spot positions have equal angular increment along the focal spot trajectory.

9. The system of claim 1, wherein the focal spot projection comprises at least one of a circle, an ellipse, a square, a rectangle, a composition of at least two closed curves intersecting at a point, a composition of a set of non-intersecting closed curves, and a spiral in the image acquisition plane.

10. The system of claim 1, wherein the focal spot projection comprises a shape including at least one of a saw tooth curve, a sine wave, a square wave, or an arbitrary curve, wherein the amplitude of the shape is defined by the volume of interest being imaged.

11. The system of claim 1, wherein the detector is stationary.

12. The system of claim 1, wherein the detector is configured to traverse in a plurality of detector positions, wherein each of the detector positions corresponds to a respective focal spot position.

13. The system of claim 12, wherein the detector positions yield the detector trajectory defining a two dimensional detector projection in the image acquisition plane.

14. An imaging system for scanning a volume of interest in an object, the system comprising:
a radiation source configured to traverse in a plurality of focal spot positions yielding a plurality of focal spot trajectories, wherein each focal spot trajectory defines a two dimensional focal spot projection in an image acquisition plane, and wherein the focal spot positions comprise at least two positions at unequal distances from the image acquisition plane; and
a detector configured to acquire a plurality of acquisition images of the volume of interest in the object from the image acquisition plane, wherein the volume of interest is placed between the detector and the plurality of focal spot positions, and wherein the detector is configured to traverse in a plurality of detector positions, each of the detector positions corresponding to a respective focal spot positions,
wherein a projection of a locus of points in the object on the detector remains stationary during the scan by adjusting the focal spot trajectory and a detector trajectory.

15. The system of claim 14, wherein the detector positions yield the detector trajectory defining a two dimensional detector projection in the image acquisition plane.

16. The system of claim 14, wherein the focal spot positions are spaced equally on the focal spot trajectory.

17. The system of claim 14, wherein the focal spot positions have equal angular increment along the focal spot trajectory.

18. The system of claim 14, wherein the focal spot projection comprises at least one of a circle, an ellipse, a square, a rectangle, a composition of at least two closed curves intersecting at a point, a composition of a set of non-intersecting closed curves, and a spiral in the image acquisition plane.

19. The system of claim 14, wherein the focal spot projection comprises a shape including at least one of a saw tooth curve, a sine wave, a square wave, or an arbitrary curve, wherein the amplitude of the shape is defined by the volume of interest being imaged.

20. An imaging system for scanning a volume of interest in an object, the system comprising:
a radiation source configured to traverse in a plurality of focal spot positions yielding a plurality of focal spot trajectories, wherein each focal spot trajectory defines a two dimensional focal spot projection in an image acquisition plane, and wherein the focal spot positions comprise at least two positions at unequal distances from the image acquisition plane;
a detector configured to acquire a plurality of acquisition images of the volume of interest in the object from the image acquisition plane, wherein the volume of interest is placed between the detector and the plurality of focal spot positions, wherein a projection of a locus of points in the object on the detector remains stationary during the scan by adjusting the focal spot trajectory and/or a detector trajectory;
a system controller operably coupled to the source;
a detector configured to acquire a plurality of acquisition images of the volume of interest in the object from the image acquisition plane, wherein the volume of interest is placed between the detector and the plurality of focal spot positions;
a motor controller configured to displace at least one of the source, and the detector;
a processor operably coupled to the detector configured to receive the plurality of projection images and to form one or more reconstructed slices representative of the volume of interest being imaged; and
an operator workstation operably coupled to the processor configured to display the one or more reconstructed slices.

21. The system of claim 20, wherein the detector is configured to traverse in a plurality of detector positions, wherein each of the detector positions corresponds to a respective focal spot position.

22. The system of claim 21, wherein the detector positions yield the detector trajectory defining a two dimensional detector projection in the image acquisition plane.

23. A radiological imaging system comprising:
a detector extending generally in a plane and configured to receive radiation attenuated by a subject of interest; and
a radiation source configured to direct radiation toward the detector through a subject of interest, the source being movable during imaging sequences in three dimensions with respect to the plane of the detector and wherein the source is configured to move in a plurality of focal spot positions,
wherein the detector is configured to acquire a plurality of acquisition images of a volume of interest in the subject, wherein the volume of interest is placed between the detector and the plurality of focal spot positions, wherein a projection of a locus of points in the object on the detector remains stationary during the scan by adjusting the focal spot trajectory and/or a detector trajectory.

24. The system of claim 23, wherein the source traces a two dimensional source projection in an image acquisition plane.

25. The system of claim 24, wherein the source is configured to move in first and second dimensions generally parallel to the plane of the detector and in a third dimension generally perpendicular to the plane of the detector.

26. The system of claim 23, wherein the detector is configured to move during imaging sequences to trace a two dimensional detector projection in an image acquisition plane.

27. The system of claim 26, wherein the detector is configured to move during imaging sequences in first and second dimensions in the plane of detector, and in a third dimension to vary the distance between the source and the detector.

28. A radiological imaging system comprising:
a detector extending generally in a plane and configured to receive radiation attenuated by a subject of interest; and
a radiation source configured to direct radiation toward the detector through a subject of interest, the source being movable during imaging sequences in first and second dimensions generally parallel to the plane of the detector and in a third dimension generally perpendicular to the plane of the detector and wherein the source is configured to move in a plurality of focal spot positions,
wherein the detector is configured to acquire a plurality of acquisition images of a volume of interest in the subject, wherein the volume of interest is placed between the detector and the plurality of focal spot positions, wherein a projection of a locus of points in the object on the detector remains stationary during the scan by adjusting the focal spot trajectory and/or a detector trajectory.

29. The system of claim 28, wherein the source traces a two dimensional source projection in an image acquisition plane.

30. The system of claim 28, wherein the detector is configured to move during imaging sequences to trace a two dimensional detector projection in an image acquisition plane.

31. The system of claim 30, wherein the detector is configured to move during imaging sequences in first and second dimensions in the plane of the detector, and in a third dimension to vary the distance between the source and the detector.

32. A radiological imaging system comprising:
a detector extending generally in a plane and configured to receive radiation attenuated by a subject of interest; and
a radiation source configured to direct radiation toward the detector through a subject of interest, the source being movable during imaging sequences in first and second dimensions in the plane of the detector, and a third dimension to vary the distance between the source and the detector and wherein the source is configured to move in a plurality of focal spot positions,
wherein the detector is configured to acquire a plurality of acquisition images of a volume of interest in the subject, wherein the volume of interest is placed between the detector and the plurality of focal spot positions, wherein a projection of a locus of points in the object on the detector remains stationary during the scan by adjusting the focal spot trajectory and/or a detector trajectory.

33. The system of claim 32, wherein the source traces a two dimensional source projection in an image acquisition plane.

34. The system of claim 32, wherein the source is configured to move in first and second dimensions generally parallel to the plane of the detector and in a third dimension generally perpendicular to the plane of the detector.

35. The system of claim 32, wherein the detector is configured to move during imaging sequences to trace a two dimensional detector projection in an image acquisition plane.

36. A radiological imaging system comprising:
a detector extending generally in a plane and configured to receive radiation attenuated by a subject of interest; and
a radiation source configured to direct radiation toward the detector through the subject of interest,
wherein the detector and/or the source are movable in first and second dimensions in the plane of the detector, and in a third dimension to vary the distance between the source and the detector and wherein the source is configured to move in a plurality of focal spot positions,
wherein the detector is configured to acquire a plurality of acquisition images of a volume of interest in the subject, wherein the volume of interest is placed between the detector and the plurality of focal spot positions, wherein a projection of a locus of points in the object on the detector remains stationary during the scan by adjusting the focal spot trajectory and/or a detector trajectory.

37. The system of claim 36, wherein the source traces a two dimensional source projection in an image acquisition plane.

38. The system of claim 36, wherein the detector is configured to move during imaging sequences to trace a two dimensional detector projection in an image acquisition plane.

39. A radiological imaging system comprising:
a detector extending generally in a plane and configured to receive radiation attenuated by a subject of interest; and
at least one radiation source configured to direct radiation toward the detector through the subject of interest from a plurality of focal spot positions defining a desired two dimensional projection in an image acquisition plane, the positions being displaced from one another in first and second dimensions generally parallel with the image acquisition plane and at a distance from the image acquisition plane in a third dimension detector and wherein the source is configured to move in a plurality of focal spot positions,
wherein the detector is configured to acquire a plurality of acquisition images of a volume of interest in the subject, wherein the volume of interest is placed between the detector and the plurality of focal spot positions, wherein a projection of a locus of points in the object on the detector remains stationary during the scan by adjusting the focal spot trajectory and/or a detector trajectory.

40. The system of claim 39, wherein the detector is configured to move during imaging sequences to trace a two dimensional detector projection in an image acquisition plane.

41. A method for scanning a volume of interest in an object using an imaging system, the method comprising:
traversing a radiation source in a plurality of focal spot positions yielding a plurality of focal spot trajectories, each focal spot trajectory defining a two dimensional focal spot projection in an image acquisition plane, and the focal spot positions comprising at least two positions at unequal distances from the image acquisition;

acquiring a plurality of acquisition images of the volume of interest in the object from the image acquisition plane, the volume of interest being placed between a detector and the plurality of focal spot positions, wherein a projection of a locus of points in the object on the detector remains stationary during the scan by adjusting the focal spot trajectory and/or a detector trajectory.

42. The method of claim 41, wherein the traversing the source comprises moving along a path aligned to match the volume of interest being imaged.

43. The method of claim 41, wherein the traversing the source comprises moving along a path aligned to match a selection of features of the volume of interest being imaged.

44. The method of claim 41, wherein the traversing the source comprises traversing in at least one of a step and shoot mode and a continuous mode.

45. The method of claim 41, further comprising spacing the focal spot positions equally on the focal spot trajectory.

46. The method of claim 41, further comprising angularly incrementing the focal spot positions along the focal spot trajectory.

47. The method of claim 41, wherein the focal spot projection comprises at least one of a circle, an ellipse, a square, a rectangle, a composition of at least two closed curves intersecting at a point, a composition of a set of non-intersecting closed curves, and a spiral in the image acquisition plane.

48. The method of claim 41, wherein the focal spot projection comprises a shape including at least one of a saw tooth curve, a sine wave, a square wave, or an arbitrary curve, wherein the amplitude of the shape is defined by the volume of interest being imaged.

49. The method of claim 41, further comprising traversing the detector in a plurality of detector positions, wherein each of the detector positions corresponds to a respective focal spot position.

50. The method of claim 49, wherein the detector positions yield the detector trajectory defining a two dimensional detector projection in the image acquisition plane.

51. A method for scanning a volume of interest in an object using an imaging system, the method comprising:
traversing a radiation source in a plurality of focal spot positions yielding a plurality of focal spot trajectories, each focal spot trajectory defining a two dimensional focal spot projection in an image acquisition plane, and the focal spot positions comprising at least two positions at unequal distances from the image acquisition plane; and traversing a detector in a plurality of detector positions, each of the detector positions corresponding to a respective focal spot position, the volume of interest being placed between the detector and the plurality of focal spot positions, wherein a projection of a locus of points in the object on the detector remains stationary during the scan by adjusting the focal spot trajectory and a detector trajectory.

52. The method of claim 51, wherein the traversing the source comprises moving along a path aligned to match the volume of interest being imaged.

53. The method of claim 51, wherein the traversing the source comprises moving along a path aligned to match a selection of features of the volume of interest being imaged.

54. The method of claim 51, further comprising spacing the focal spot positions equally on the focal spot trajectory.

55. The method of claim 51, further comprising angularly incrementing the focal spot positions along the focal spot trajectory.

56. The method of claim 51, wherein the detector positions yield the detector trajectory defining a two dimensional detector projection in the image acquisition plane.

57. A method for generating radiological image data comprising:
acquiring image data by a detector resulting from radiation impacting the detector from at least one radiation source positioned at a plurality of focal spot positions defining a desired projection in an image acquisition plane, the focal spot positions being displaced from one another in first and second dimensions generally parallel to the image acquisition plane and at a varying distance from the image acquisition plane in a third dimension; and moving the detector in a plurality of detector positions, each of the detector positions corresponding to a respective focal spot position, an object being placed between the detector and the plurality of focal spot positions, wherein a projection of a locus of points in the object on the detector remains stationary during the scan by adjusting the focal spot trajectory and a detector trajectory.

58. The method of claim 57, wherein the detector positions yield the detector trajectory defining a two dimensional detector projection in the image acquisition plane.

59. A method for generating radiological image data comprising:
positioning at least one radiation source at a plurality of positions defining a desired projection of an object in an image acquisition plane, the positions being displaced from one another in first and second dimensions generally parallel to the image acquisition plane and at a varying distance from the image acquisition plane in a third dimension; and acquiring image data by a detector resulting from radiation impacting the detector from the at least one radiation source, wherein a projection of a locus of points in the object on the detector remains stationary during the scan.

60. The method of claim 59, further comprising moving the detector in a plurality of detector positions, each of the detector positions corresponding to a respective focal spot position, the volume of interest being placed between the detector and the plurality of focal spot positions.

61. The method of claim 60, wherein the detector positions yield a detector trajectory defining a two dimensional detector projection in the image acquisition plane.

* * * * *